United States Patent
Seo et al.

(10) Patent No.: US 10,258,435 B2
(45) Date of Patent: Apr. 16, 2019

(54) REMOVABLE AND ADJUSTABLE ABUTMENT DEVICES AND METHODS OF OPERATION THEREOF

(71) Applicant: Rodo Medical, Inc., San Jose, CA (US)

(72) Inventors: Young Seo, Sunnyvale, CA (US); Jong Gil Park, Santa Clara, CA (US)

(73) Assignee: Rodo Medical, Inc., San Jose, CA (US)

( * ) Notice: Subject to any disclaimer, the term of this patent is extended or adjusted under 35 U.S.C. 154(b) by 55 days.

(21) Appl. No.: 15/337,905

(22) Filed: Oct. 28, 2016

(65) Prior Publication Data

US 2018/0116769 A1    May 3, 2018

(51) Int. Cl.
*A61C 8/00* (2006.01)
*A61C 13/265* (2006.01)

(52) U.S. Cl.
CPC .......... *A61C 8/0089* (2013.01); *A61C 8/0048* (2013.01); *A61C 8/0053* (2013.01); *A61C 13/2656* (2013.01); *A61C 2201/007* (2013.01)

(58) Field of Classification Search
CPC ... A61C 8/0063; A61C 8/0062; A61C 8/0065; A61C 8/0071; A61C 8/0089; A61C 8/0048; A61C 8/0053; A61C 13/2656; A61C 2201/007
See application file for complete search history.

(56) References Cited

U.S. PATENT DOCUMENTS

| | | | |
|---|---|---|---|
| 4,431,113 A * | 2/1984 | Sims, Jr. | H05K 5/03 220/3.8 |
| 5,470,230 A | 11/1995 | Daftary et al. | |
| 6,710,314 B2 | 3/2004 | Riess et al. | |
| 8,047,844 B2 | 11/2011 | Seo | |
| 8,109,764 B2 | 2/2012 | Seo | |
| 8,221,118 B2 | 7/2012 | Seo | |
| 8,317,515 B2 | 11/2012 | Seo et al. | |
| 8,403,668 B2 | 3/2013 | Seo | |
| 8,491,303 B2 | 7/2013 | Seo et al. | |
| 8,651,864 B2 | 2/2014 | Seo et al. | |

(Continued)

FOREIGN PATENT DOCUMENTS

| WO | WO 2003/030768 | 4/2003 |
|---|---|---|
| WO | WO 2017/080845 | 5/2018 |

OTHER PUBLICATIONS

Wilson, T. "The positive relationship between excess cement and peri-implant disease: a prospective clinical endoscopic study," *Journal of Periodontology*, 80:1388-1392, Sep. 2009.

*Primary Examiner* — Heidi M Eide
(74) *Attorney, Agent, or Firm* — Levine Bagade Han LLP

(57) ABSTRACT

Apparatus and methods for adjustably retaining an oral appliance to an abutment assembly are disclosed. In one variation, a securement apparatus can comprise a sleeve having a sleeve frame and a number of locking flaps. The sleeve can define a lumen therethrough for positioning upon an abutment assembly. The locking flaps can have varying length dimensions and can project radially inward or outward relative to the sleeve frame. The outward flaps can lock against surface features defined along an inner surface of a coping coupled to the oral appliance and the inward flaps can lock against surface features defined along a portion of the abutment assembly. The sleeve can release the oral appliance from the abutment assembly when the locking flaps of the sleeve are actuated by an actuation unit.

10 Claims, 14 Drawing Sheets

(56) References Cited

U.S. PATENT DOCUMENTS

| | | |
|---|---|---|
| 8,678,822 B2 | 3/2014 | Seo |
| 8,845,329 B2 | 9/2014 | Seo |
| 9,168,111 B2 | 10/2015 | Seo et al. |
| 2003/0082499 A1* | 5/2003 | Halldin ................ A61C 8/0001 433/173 |
| 2012/0202173 A1* | 8/2012 | Seo ...................... A61C 8/0025 433/220 |
| 2013/0177873 A1 | 7/2013 | Seo et al. |
| 2014/0272792 A1 | 9/2014 | Haralampopoulos et al. |

\* cited by examiner

PRIOR ART

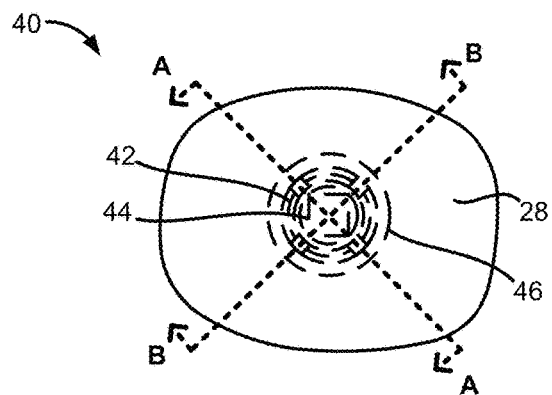
FIG. 8A
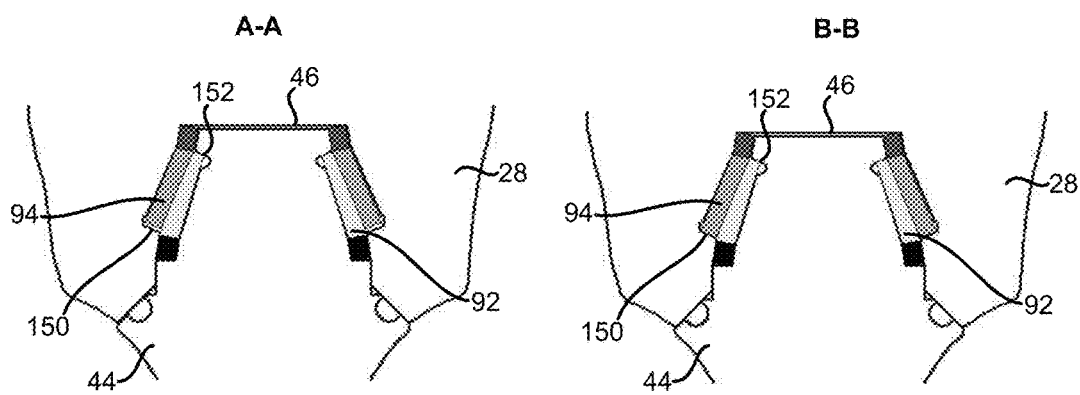
FIG. 8B   FIG. 8C

REMOVABLE AND ADJUSTABLE ABUTMENT DEVICES AND METHODS OF OPERATION THEREOF

FIELD OF THE INVENTION

The present invention relates to methods and apparatus for retaining one or more dental prostheses in a mouth of a user. More particularly, the present invention relates to methods and apparatus for retaining one or more dental prostheses in a manner which facilitates placement and removal of a dental prosthesis from a dental abutment.

BACKGROUND OF THE INVENTION

The use of dental prostheses to replace missing or damaged teeth is commonplace. Typically, artificial roots, or implants, are implanted into the bone of the patient's jaw and are used to provide structural support to an intermediate abutment. One or more artificial replacement teeth or crowns are then fastened to the abutment typically by cement or screws.

FIGS. 1A to 1D illustrate partial cross-sectional side views of one example of a typical crown being implanted within a mouth of a patient. Depending upon the number of teeth to be replaced, one or more holes may be bored within the bone of the jaw. As shown in FIG. 1A, a portion of the patient's gums or gingiva 14 may be cut open to expose the underlying bone 10, e.g., maxilla or mandible, into which a drill bit 16 may be used to bore open a hole 12. An anchoring dental implant 18, optionally threaded, may be implanted within the hole 12 and covered by gingiva 14 to allow for healing and for the implant 18 to take hold within the bone 10, as shown in FIG. 1B.

Once the implant 18 has been desirably positioned within bone 10, an abutment assembly 20 may be securely attached to implant 18, e.g., by a threaded pin 22 coupling to an implant receiving well 26 defined within implant 18 such that abutment 24, which defines a portion projecting through gingiva 14, as shown in FIG. 1C. With abutment assembly 20 secured to implant 18, an oral appliance 28, such as a crown, which defines an appliance opening 30 may be secured upon abutment 24 by utilizing a number of securement mechanisms, such as cement or a fastener such as a screw. Other securement mechanisms have also included interference fitting, such as with a cross-bar or O-ring type attachment, magnets, etc.

Because the implant, abutment, and oral appliance are subjected to high compressive and shear forces, initial positioning of the oral appliance is important not only to provide adequate structural support but also to ensure patient comfort. However, while utilizing cement to attach the oral appliance to the abutment initially allows for aligning the oral appliance more naturally with the dentition of the patient, the tolerance for mistakes is low once the cement has set because of the difficulty and expense in removing a cemented oral appliance from the abutment. In addition, dental professionals often apply too much cement to the area surrounding the abutment. Such excess cement has been shown in studies to be associated with high rates of peri-implant disease in patients receiving certain oral appliances. See Wilson, Thomas G. *The positive relationship between excess cement and peri-implant disease: a prospective clinical endoscopic study.* Journal of Periodontology 2009: 80: 1388-1392.

Screw-type retention devices may also provide for good securement of the oral appliance to the abutment, but occlusal contact within the patient dentition is often misaligned resulting in a variety of complications. For instance, misaligned crowns result in a compromised occlusal table which in turn may lead to chipping of the crowns as well as poor aesthetic appearance of the patient's dentition.

Accordingly, there exists a need for methods and devices which can effectively and efficiently facilitate not only the retention of oral appliances, such as crowns, bridges, or dentures, along the dentition of a patient but also the removal and/or repositioning of such oral appliances without causing unnecessary damage to the oral appliance.

SUMMARY OF THE INVENTION

The assemblies described provide for mechanisms and methods to facilitate the seating, adjustment or removal of an oral appliance, such as a crown, bridge or dentures, from an abutment assembly. In utilizing the abutment assemblies described herein, an anchoring implant may be bored into the bones within the mouth of the patient to provide for the structural support of the abutment assembly. Moreover, the implants and abutment assemblies described herein may be utilized in any number of locations within the mouth of the patient, for instance, along the maxilla or mandible or other locations within the body which may benefit from an adjustable or removable abutment assembly as described herein. Additionally, although some of the examples illustrate the placement and/or removal of crowns, various other prostheses for placement within or along the patient dentition may be utilized with the devices described herein and are not intended to be limited to use with crowns.

A securement apparatus for adjustably retaining an oral appliance is disclosed. The securement apparatus can include a sleeve comprising a sleeve frame and a plurality of locking flaps including a first set of locking flaps and a second set of locking flaps. The sleeve can define a lumen therethrough for positioning upon an abutment. The first set of locking flaps can project radially inward relative to the sleeve frame to lock against the abutment. The second set of locking flaps can project radially outward relative to the sleeve frame to lock against the oral appliance. At least one of the first set of locking flaps and the second set of locking flaps comprise between one locking flap and twenty locking flaps. In addition, at least one of the first set of locking flaps and the second set of locking flaps may comprise locking flaps of different lengths, or may be of the same length.

In one variation, the first set of locking flaps can include four locking flaps having a first pair of locking flaps of the same length and a second pair of locking flaps of a different length than the length of the first pair of locking flaps. In this variation or other variations, the second set of locking flaps can include four locking flaps having a first pair of locking flaps of the same length and a second pair of locking flaps of a different length than the length of the first pair of locking flaps.

A securement apparatus for adjustably retaining an oral appliance is disclosed. The securement apparatus can include a sleeve comprising a sleeve frame, a first locking flap, and a second locking flap. The sleeve can define a lumen therethrough for positioning upon an abutment. The first locking flap can have a first length dimension and project radially outward relative to the sleeve frame for locking against the oral appliance. The second locking flap can have a second length dimension and project radially outward relative to the sleeve frame for locking against the oral appliance. The first length dimension can be different from the second length dimension.

Another variation of the securement apparatus can include a sleeve comprising a sleeve frame, a first locking flap, and a second locking flap. The sleeve can also define a lumen therethrough for positioning upon an abutment. The first locking flap can have a first length dimension and project radially inward relative to the sleeve frame for locking against the abutment. The second locking flap can have a second length dimension and project radially inward relative to the sleeve frame for locking against the abutment. The first length dimension can be different from the second length dimension.

A securement assembly for adjustably retaining an oral appliance in an oral cavity is also disclosed. The securement assembly can include an abutment assembly and a sleeve comprising a sleeve frame, a first locking flap, and a second locking flap. The first locking flap can have a first length dimension and the second locking flap can have a second length dimension different from the first length dimension. The abutment assembly can comprise a frustum having a frustum surface configured to receive a lumen defined by the sleeve. The abutment assembly can be defined by an undercut extending radially inward relative to the frustum surface. The first locking flap and the second locking flap can project radially inward relative to the sleeve frame for locking against an edge of the abutment assembly adjoining the undercut.

Another variation of the securement assembly can include a coping and a sleeve comprising a sleeve frame, a first locking flap, and a second locking flap. The first locking flap can have a first length dimension and the second locking flap can have a second length dimension. The first length dimension can be different from the second length dimension. The coping can have an inner surface. The coping can be defined by an undercut extending radially outward relative to the center of the coping and into the inner surface. At least one of the first locking flap and the second locking flap can project radially outward relative to the sleeve frame for locking against an edge of the undercut.

A method of adjustably retaining an oral appliance in an oral cavity is also disclosed. The method can include securing an abutment assembly in an oral cavity of a patient such that an abutment portion extends beyond the gingiva of the patient. The method can also include coupling a sleeve comprising a sleeve frame, a first locking flap, and a second locking flap to the abutment portion. The first locking flap can have a first length dimension and the second locking flap can have a second length dimension different from the second length dimension. The first locking flap and the second locking flap can project radially outward relative to the sleeve frame. The method can also include positioning the oral appliance upon the abutment portion and locking the oral appliance to the abutment assembly when at least one of the first locking flap and the second locking flap pushes against an edge of a coping attached to the oral appliance.

BRIEF DESCRIPTION OF THE DRAWINGS

FIG. 8A illustrates a top plan view of a variation of a prosthesis assembly.

FIG. 8B illustrates a cross-sectional side view of a variation of a prosthesis assembly taken along line A-A shown in FIG. 8A.

FIG. 8C illustrates a cross-sectional side view of a variation of the prosthesis assembly taken along line B-B shown in FIG. 8A.

DETAILED DESCRIPTION OF THE INVENTION

In positioning and securing an oral appliance, such as a crown, bridge, or denture, within the mouth of a patient, the retaining assemblies described herein allow not only for secure attachment but also for adjustment of the oral appliance along the patient's dentition. The assemblies described also provide for mechanisms and methods to facilitate the entire removal of the oral appliance from an abutment assembly. In utilizing the abutment assemblies described herein, any number of typical anchoring implants may be bored into the bones within the mouth of the patient to provide for the structural support of the abutment assembly. Moreover, the implants and abutment assemblies described herein may be utilized in any number of locations within the mouth of the patient, for instance, along the maxilla or mandible or other locations within the body which may benefit from an adjustable abutment assembly as described herein.

Figure 1A:
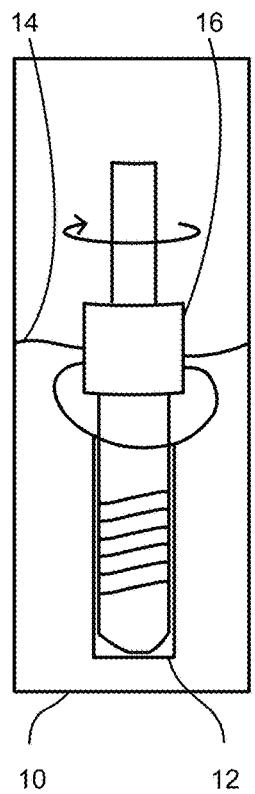
FIGS. 1A to 1D illustrate partial cross-sectional profiles of an implant placed in an oral cavity of a patient and attaching an oral appliance thereto.
Figure 1B:
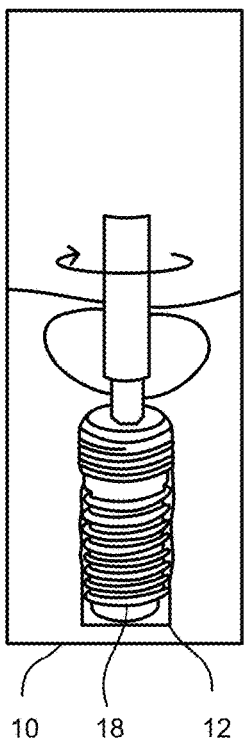
Figure 1C:
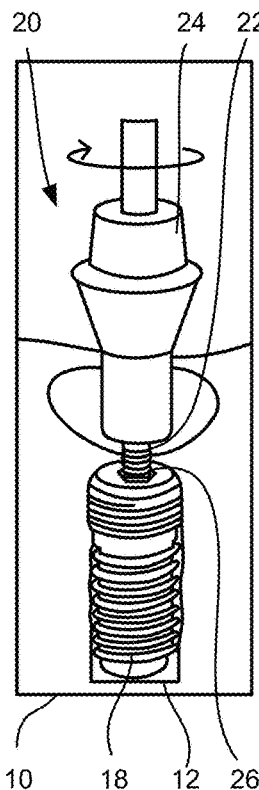
Figure 1D:
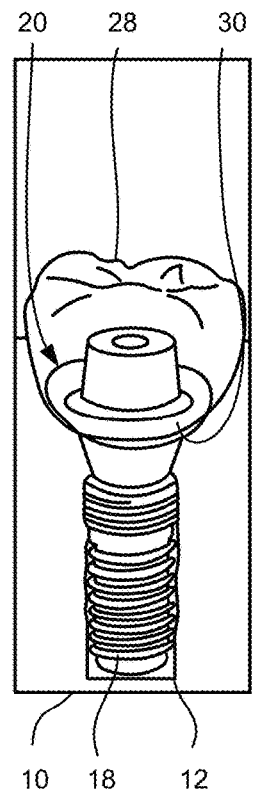
Figure 2:
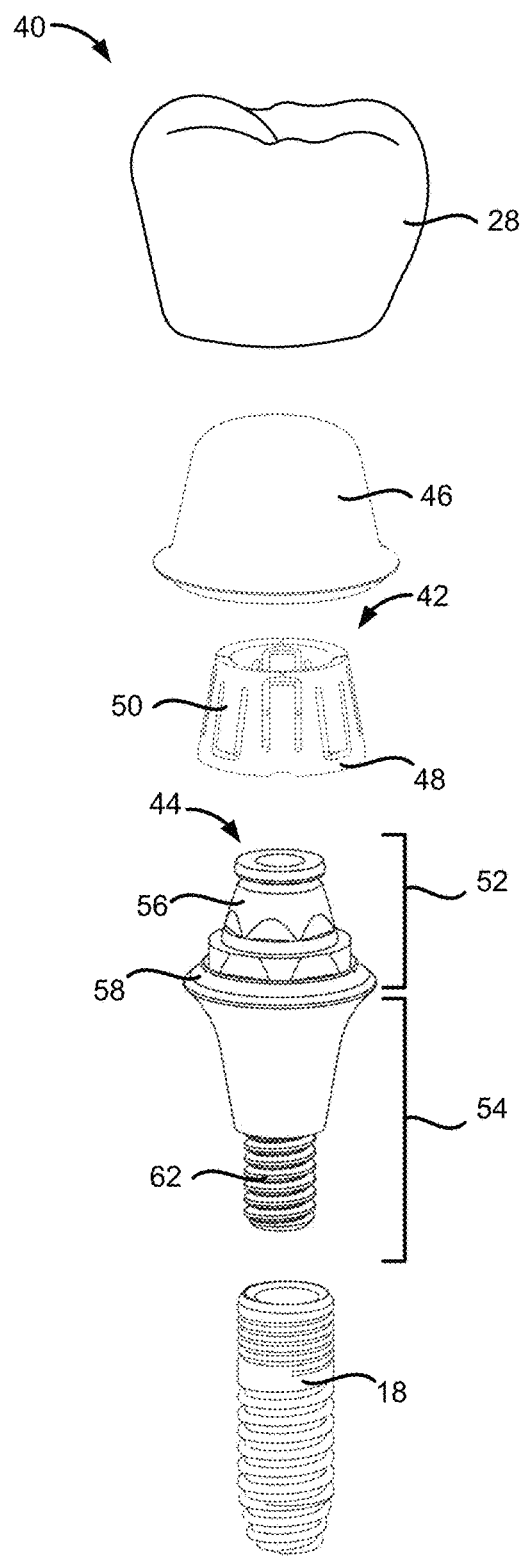
FIG. 2 illustrates an exploded view of a variation of a prosthesis assembly.

Turning now to FIG. 2, one example of a prosthesis assembly 40 is illustrated as having a sleeve 42, an abutment assembly 44, and a coping 46. The prosthesis assembly 40 can also include an oral appliance 28, such as a crown, a bridge, or dentures, the anchoring implant 18, or any combination thereof. The sleeve 42 can have a sleeve frame 48 and one or more locking flaps 50 which extend longitudinally along a lateral surface of the sleeve 42. The sleeve 42 will be discussed in more detail in the sections that follow.

The abutment assembly 44 can include an upper abutment portion 52 and a lower abutment portion 54. The upper abutment portion 52 can have a frustum 56, a seal 58, or any combination thereof. The lower abutment portion 54 can have a threaded pin 62 for attaching to the anchoring implant 18. In another variation, the threaded pin 62 can be coupled to a pre-existing root of a patient's tooth, such as to a pulp chamber.

Portions of the abutment assembly 44 can be fabricated from any number of biocompatible materials, e.g., gold alloys, stainless steel, titanium alloys, nickel-titanium alloys, etc., and can be sized for positioning along the patient's dentition. For instance, the abutment assembly 44 can have a diameter along its widest portion ranging from, e.g., 2 mm to 10 mm, and a length ranging from, e.g., 1 mm to 15 mm. These dimensions are exemplary and are not intended to be limiting. The abutment assembly 44 can be any of the abutments or abutment retaining assemblies disclosed in U.S. patent application Ser. Nos. 14/485,430 and 14/602,062, and U.S. Pat. Nos. 8,047,844; 8,109,764; 8,317,515; 8,491,303; 8,221,118; 8,403,668; 8,651,864; 8,678,822; 8,845,329; and 9,168,111, all of which are herein incorporated by reference in their entireties.

The frustum 56 can be a segment of the upper abutment portion 52 having a frustoconical or tapered shape. The frustum 56 can receive the sleeve 42 when the sleeve 42 is curled into a tapered configuration. The frustum 56 can be defined in between the seal ring 58 and the top of the abutment assembly 44. In one variation, the frustum 56 can have a smooth or unabraded surface. In another variation, the frustum 56 can have a rough or abraded surface. The upper abutment portion 52, including the frustum 56, the seal 58, or any combination thereof can extend beyond the gingiva 14 of the patient when the abutment assembly 44 is secured onto the anchoring implant 18.

The seal 58 can be formed to have any variety of configurations to conform to the upper abutment portion 52. The seal 58 can serve as a cushioning layer or interface between the coping 46 and the abutment assembly 44. The seal 58 can be fabricated from any number of biocompatible materials or biocompatible elastomers, e.g., silicone, polyurethane, poly(vinyl chloride), etc.

The coping 46 can be a cap or covering serving as an accommodation or platform for the oral appliance 28. In the variation shown in FIG. 2, the coping 46 can be shaped substantially as a thimble or frustoconic having rounded edges. The oral appliance 28 can be attached to an outside surface of the coping 46 by a biocompatible adhesive such as cement, ceramic fusion, or an interference fit. In one variation, the oral appliance 28 and the coping 46 can be fabricated or made as one component. The inner surface of the coping 46 can be shaped or defined to accommodate fitting over or onto the upper abutment portion 52. As shown in FIG. 2, the inner surface of the coping 46 can also be shaped or defined to accommodate fitting over the sleeve 42 and the upper abutment portion 52.

Figure 3A:
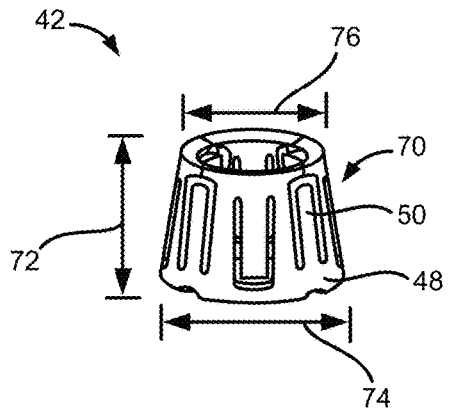
FIG. 3A illustrates a variation of a sleeve of the prosthesis assembly in a low-profile configuration.

FIG. 3A illustrates a variation of the sleeve 42 of the prosthesis assembly 40 in a low-profile configuration 70. The sleeve 42 can be considered to be in the low-profile configuration 70 when the locking flaps 50 are straightened or flush with respect to the lateral surface of the sleeve frame 48. In another variation, the sleeve 42 can be considered to be in the low-profile configuration 70 when the locking flaps 50 do not project radially inward or outward relative to the lateral surface of the sleeve frame 48. In other variations, the sleeve 42 can be considered to be in the low-profile configuration 70 when the locking flaps 50 project less radially inward or outward relative to the lateral surface of the sleeve frame 48 than the sleeve 42 in the locking configuration 90 (see FIG. 5A).

FIG. 3A also illustrates that the sleeve 42 can have a height dimension 72, a base diameter 74, and a top diameter 76. The height dimension 72 can range from, e.g., 1 mm to 15 mm. The base diameter 74 can range from, e.g., 1 mm to 10 mm. The top diameter 76 can range from, e.g., 0.5 mm to 10 mm.

Figure 3B:
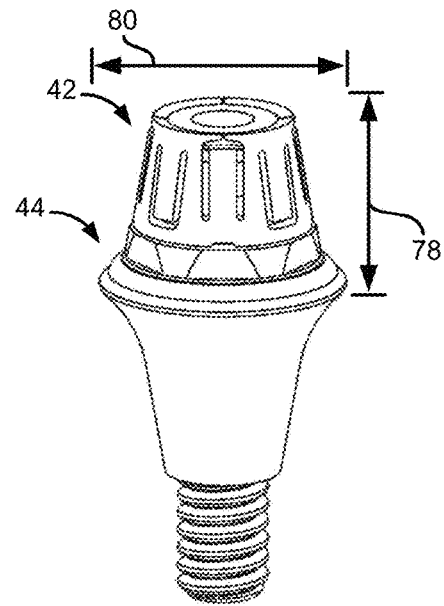
FIG. 3B illustrates the sleeve of FIG. 3A positioned on an abutment assembly.

FIG. 3B illustrates the sleeve 42 positioned on a variation of the abutment assembly 44. The sleeve 42 can be positioned on the upper abutment portion 52 around the frustum 56 of the abutment assembly 44. The upper abutment portion 52 can have a height dimension 78 and an abutment diameter 80. The height dimension 78 of the upper abutment portion 52 can range from, e.g., 1 mm to 20 mm.

The abutment diameter 80 can be the diameter of the abutment assembly 44 at its widest portion, for example, at the interface between the upper abutment portion 52 and the lower abutment portion 54. The abutment diameter 80 can range from, e.g., 2 mm to 12 mm.

The sleeve 42 and abutment assembly 44 shown in FIGS. 3A and 3B can be used to secure an oral appliance 28 configured to replace a molar, a bicuspid, a cuspid, or an incisor. For example, the sleeve 42 and abutment assembly 44 shown in FIGS. 3A and 3B can be used to secure an oral appliance 28 configured to replace a second bicuspid.

Figure 4A:
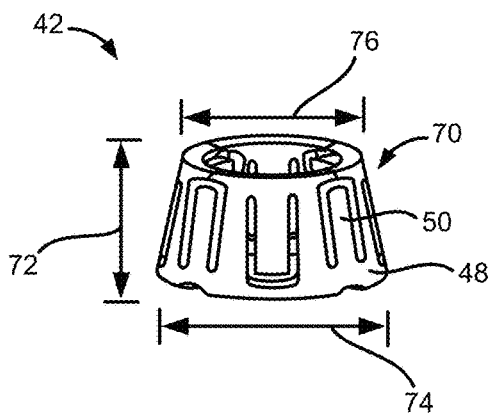
FIG. 4A illustrates another variation of a sleeve of the prosthesis assembly in a low-profile configuration.

FIG. 4A illustrates another variation of the sleeve 42 of the prosthesis assembly 40 in the low-profile configuration 70. FIG. 4A illustrates that the sleeve 42 can have a height dimension 72.

Figure 4B:
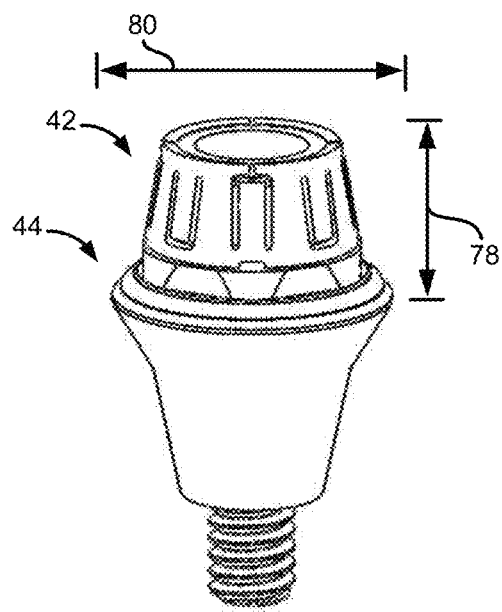
FIG. 4B illustrates the sleeve of FIG. 4A positioned on an abutment assembly.

FIG. 4B illustrates another variation of the abutment assembly 44. The upper abutment portion 52 can have a height dimension 78. The sleeve 42 and abutment assembly 44 shown in FIGS. 4A and 4B can be used to secure an oral appliance 28 configured to replace a molar or a bicuspid. For example, the sleeve 42 and abutment assembly 44 shown in FIGS. 4A and 4B can be used to secure an oral appliance 28 configured to replace a first molar.

The sleeve 42 can be fabricated from or comprise a shape memory material such as a shape memory metal or metal alloy, a shape memory polymer, or a composite thereof. In these and other variations, the sleeve 42 can be fabricated from or comprise stainless steel, nickel-titanium alloys such as Nitinol, titanium, or a composite thereof.

Figure 5A:
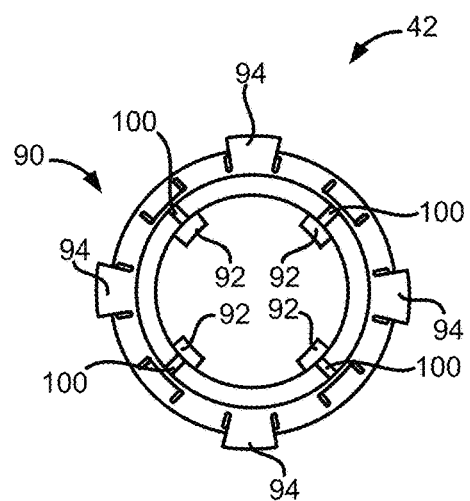
FIG. 5A illustrates a top plan view of a variation of a sleeve in a locking configuration.

FIG. 5A illustrates a top plan view of a variation of the sleeve 42 in a locking configuration 90. The sleeve 42 can be considered to be in the locking configuration 90 when one or more locking flaps 50 project or curve radially inward or outward relative to the lateral surface of the sleeve frame 48. The locking flaps 50 can include one or more inward flaps 92 and one or more outward flaps 94. One sleeve 42 can have both inward flaps 92 and outward flaps 94 arranged in an alternating manner. The locking flaps 50, including the inward flaps 92 and the outward flaps 94, can be slotted cut-outs defined along the lateral surface of the sleeve 42.

The inward flaps 92 can be a type of locking flap 50 configured to project or bend radially inward relative to the lateral surface of the sleeve frame 48. The outward flaps 94 can be a type of locking flap 50 configured to project or bend radially outward relative to the lateral surface of the sleeve frame 48.

Figure 5B:
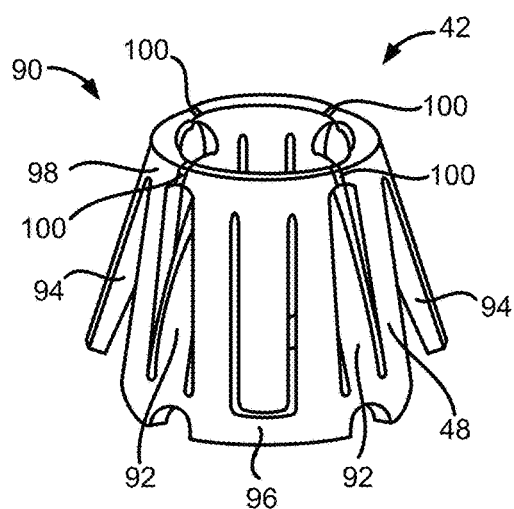
FIG. 5B illustrates a perspective view of the sleeve of FIG. 5A in the locking configuration.

FIG. 5B illustrates a perspective view of the sleeve 42 in the locking configuration 90. FIG. 5B shows that the inward flaps 92 can be connected to or contiguous with a lower portion 96 of the sleeve frame 48. In addition, FIG. 5B shows that the outward flaps 94 can be connected to or contiguous with an upper portion 98 of the sleeve frame 48. In other variations not shown in the figures but contemplated by the disclosure, the inward flaps 92 can be connected to or contiguous with the upper portion 98 of the sleeve frame 48 and the outward flaps 94 can be connected to or contiguous with the lower portion 96 of the sleeve frame 48.

When the sleeve 42 is folded into a tapered or frustoconical shape, the diameter of the lower portion 96 of the sleeve 42 can be greater than the diameter of the upper portion 98 of the sleeve 42. FIG. 5B also illustrates that the sleeve 42 can have one or more gaps 100 defined along the upper portion 98 of the sleeve frame 48. The gaps 100 can be spaces or non-contiguous regions along the upper portion 98 of the sleeve frame 48.

FIGS. 5A and 5B show a variation of the sleeve 42 having four gaps 100 along the upper portion 98 of the sleeve frame 48. In some variations, the gaps 100 can be located along the same longitudinal section as each of the inward flaps 92. In other variations, the gaps 100 can be located along the same longitudinal section as each of the outward flaps 94 or some of the inward flaps 92 or outward flaps 94.

Figure 6:
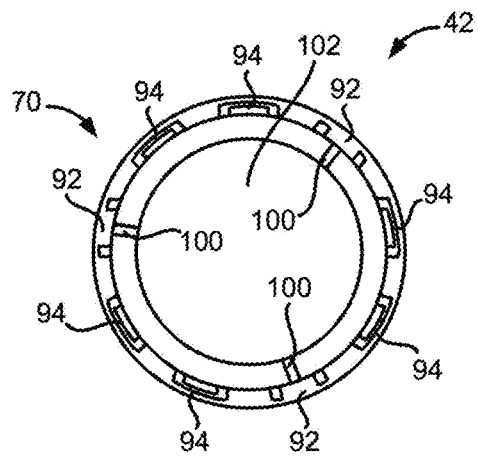
FIG. 6 illustrates a top plan view of a variation of a sleeve in a low-profile configuration.

FIG. 6 illustrates a top plan view of another variation of the sleeve 42 in the low-profile configuration 70. FIG. 6 shows that any of the inward flaps 92 or the outward flaps 94 can be immediately adjacent to two inward flaps 92, two outward flaps 94, or an inward flap 92 and an outward flap 94. For example, as illustrated in FIG. 6, each of the inward flaps 92 can be arranged in between two outward flaps 94 and each of the outward flaps 94 can be arranged in between another outward flap 94 and an inward flap 92.

The tapered sleeve 42 can be heat treated when in the low-profile configuration 70 to retain its shape memory of the low-profile configuration 70 with all of the locking flaps 50 collapsed and flush with the lateral surface of the sleeve frame 48. The tapered sleeve 42 can then be allowed to cool and manually formed into the locking configuration 90. The tapered sleeve 42 can then be locked onto the abutment assembly 44 when the sleeve 42 is in the locking configuration 90 and an oral appliance 28 can also be placed on top of the abutment assembly 44 covered by the sleeve 42. When the time comes for a dental professional to remove the oral appliance 28 from the abutment assembly 44, the sleeve 42 can be heated beyond a threshold temperature (e.g., the shape memory transformation temperature of the sleeve 42) and the sleeve 42 can once again achieve its low-profile configuration 70 to allow the oral appliance 28 to be lifted off the sleeve 42.

FIGS. 5A and 6 also illustrate that the sleeve 42 can define or form a lumen 102 when the sleeve 42 is folded or curled into a tapered or frustoconical shape. The sleeve 42 can be in the low-profile configuration 70 when at least the inward flaps 92 do not project or extend into the lumen 102 or the inward flaps 92 retract, at least partially, out of the lumen 102. In other variations, the sleeve 42 can be in the low-profile configuration 70 when a portion of the inward flaps 92 retract out of the lumen 102 to an extent that allows a dental professional to remove the sleeve 42 from the abutment assembly 44. The sleeve 42 can also be in the low-profile configuration 70 when the outward flaps 94 do not project radially outward relative to the lateral surface of the sleeve frame 48 or when portions of the outward flaps 94 collapse radially inward to an extent that allows a dental professional to remove the coping 46 covering the sleeve 42.

Figure 7A:
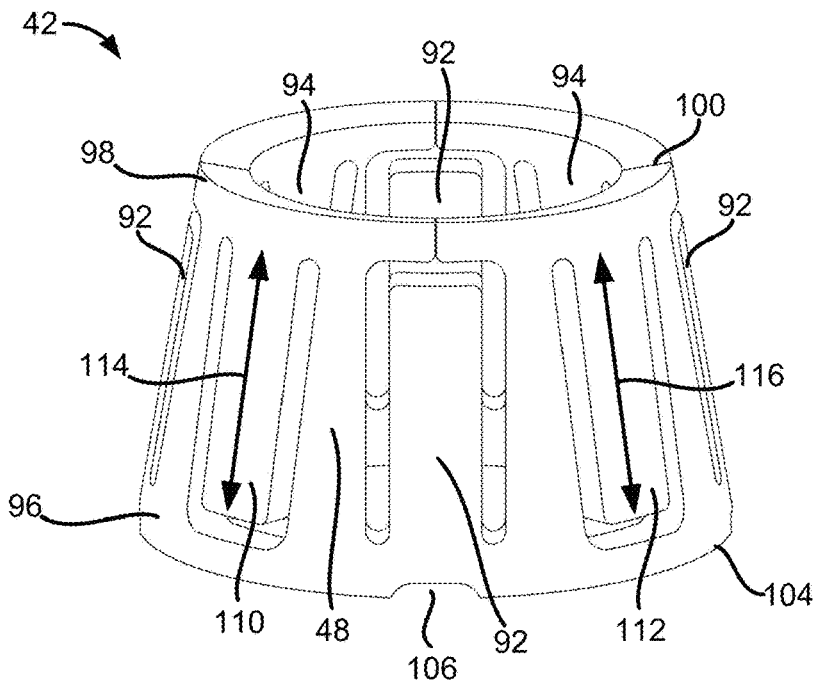
FIG. 7A illustrates a variation of a sleeve.
Figure 7B:
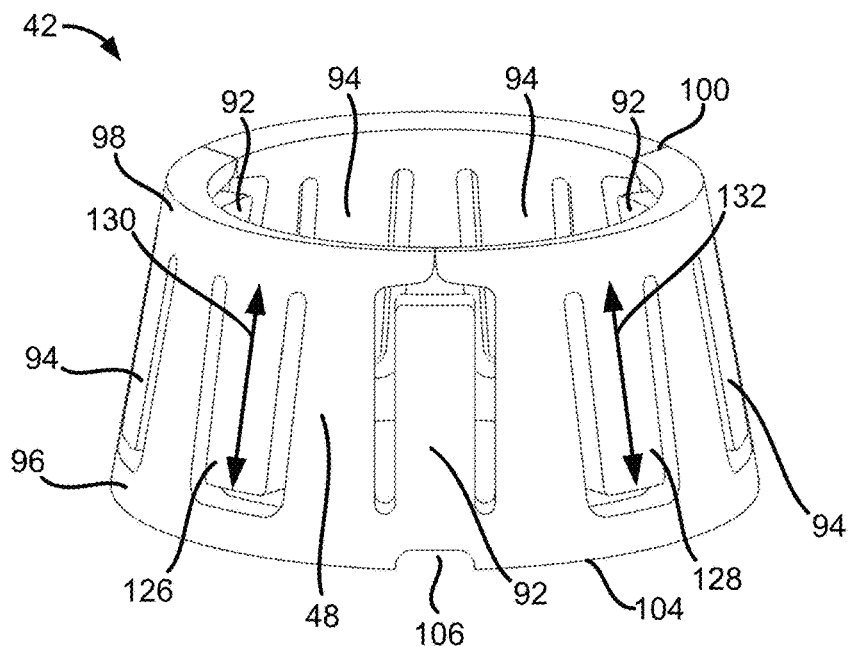
FIG. 7B illustrates another variation of a sleeve.

FIGS. 7A and 7B illustrate variations of the sleeve 42. FIGS. 7A and 7B illustrate that the locking flaps 50 can have differing length dimensions. FIG. 7A illustrates that a variation of the sleeve 42 can have eight total locking flaps 50 with four inward flaps 92 and four outward flaps 94. The locking flaps 50 can be arranged in an alternating manner with each inward flap 92 adjacent to two outward flaps 94 and each outward flap 94 adjacent to two inward flaps 92. FIG. 7A also illustrates that the outward flaps 94 can include a first outward flap 110 and a second outward flap 112. The first outward flap 110 can be separated from the second outward flap 112 by an inward flap 92.

Additionally, the sleeve frame 48 can have a bottom edge 104. The bottom edge 104 can be defined by one or more cutouts 106 along the bottom edge 104. The cutouts 106 can be substantially shaped as half or partial-circles, half or partial-ovals, rectangles, triangles, trapezoids, or a combination thereof.

The first outward flap 110 can have a first length dimension 114 and the second outward flap 112 can have a second length dimension 116. The first length dimension 114 can be a longitudinal length of the first outward flap 110. The first length dimension 114 can be measured from the base of the first outward flap 110 to the tip or terminal end of the first outward flap 110. The base of the first outward flap 110 can be the portion of the first outward flap 110 connected to the upper portion 98 of the sleeve frame 48.

The second length dimension 116 can be a longitudinal length of the second outward flap 112. The second length dimension 116 can be measured from the base of the second outward flap 112 to the tip or terminal end of the second outward flap 112. The base of the second outward flap 112 can be the portion of the second outward flap 112 connected to the upper portion 98 of the sleeve frame 48.

The second length dimension 116 can be greater than the first length dimension 114. The difference between the second length dimension 116 and the first length dimension 114 can be between, e.g., 0.001 mm and 14.0 mm. FIG. 7A illustrates that the sleeve 42 can have two outward flaps 94 having the first length dimension 114 and two other outward flaps 94 having the second length dimension 116. In the variation shown in FIG. 7A, the inward flaps 92 can have the same or substantially equivalent length dimension. In other variations not shown in the figures but contemplated by this disclosure, the inward flaps 92 can have differing length dimensions. Each of the inward flaps 92 can have a gap 100 defined along the upper portion 98 of the sleeve frame 48 at the terminal end of the inward flaps 92.

Although not shown in the figures, another variation of the sleeve 42 is contemplated by this disclosure that can have eight total locking flaps 50 with four inward flaps 92 and four outward flaps 94. The locking flaps 50 can be arranged in an alternating manner with each inward flap 92 adjacent to two outward flaps 94 and each outward flap 94 adjacent to two inward flaps 92. The inward flaps 92 can include a first inward flap and a second inward flap. The first inward flap can be separated from the second inward flap by an outward flap 94.

The first inward flap can have a first length dimension and the second inward flap can have a second length dimension. The first length dimension can be a longitudinal length of the first inward flap. The first length dimension can be measured from the base of the first inward flap to the tip or terminal end of the first inward flap. The base of the first inward flap can be the portion of the first inward flap connected to the lower portion 96 of the sleeve frame 48.

The second length dimension can be a longitudinal length of the second inward flap. The second length dimension can be measured from the base of the second inward flap to the tip or terminal end of the second inward flap. The base of the second inward flap can be the portion of the second inward flap connected to the lower portion 96 of the sleeve frame 48.

The second length dimension can be greater than the first length dimension. The difference between the second length dimension and the first length dimension can be between, e.g., 0.001 mm and 14.0 mm. The sleeve 42 can have two inward flaps 92 having the first length dimension and two other inward flaps 92 having the second length dimension. In one variation, the outward flaps 94 can have the same or substantially equivalent length dimension. In other variations, the outward flaps 94 can have differing length dimensions. Each of the inward flaps 92, including the first inward flap and the second inward flap, can have a gap 100 defined along the upper portion 98 of the sleeve frame 48 at the terminal end of the inward flaps 92.

FIG. 7B illustrates that another variation of the sleeve 42 can have nine total locking flaps 50 with three inward flaps 92 and six outward flaps 94. The locking flaps 50 can be arranged so that each inward flap 92 is adjacent to two outward flaps 94 and each outward flap 94 is adjacent to one inward flap 92 and one other outward flap 94. FIG. 7B also illustrates that the outward flaps 94 can include a first outward flap 126 and a second outward flap 128.

The first outward flap 126 can have a first length dimension 130 and the second outward flap 128 can have a second length dimension 132. The first length dimension 130 can be a longitudinal length of the first outward flap 126. The first length dimension 130 can be measured from the base of the first outward flap 126 to the tip or terminal end of the first outward flap 126. The base of the first outward flap 126 can be the portion of the first outward flap 126 connected to the upper portion 98 of the sleeve frame 48.

The second length dimension 132 can be a longitudinal length of the second outward flap 128. The second length dimension 132 can be measured from the base of the second outward flap 128 to the tip or terminal end of the second outward flap 128. The base of the second outward flap 128 can be the portion of the second outward flap 128 connected to the upper portion 98 of the sleeve frame 48.

The second length dimension 132 can be greater than the first length dimension 130. The difference between the second length dimension 132 and the first length dimension 130 can be between, e.g., 0.001 mm and 14.0 mm. FIG. 7B illustrates that the sleeve 42 can have three outward flaps 94 having the first length dimension 130 and three other outward flaps 94 having the second length dimension 132. In the variation shown in FIG. 7B, the inward flaps 92 can have the same or substantially equivalent length dimension. In other variations not shown in the figures but contemplated by this disclosure, the inward flaps 92 can have differing length dimensions. Each of the inward flaps 92 can have a gap 100 defined along the upper portion 98 of the sleeve frame 48 at the terminal end of the inward flaps 92.

Although not shown in the figures, another variation of the sleeve 42 is contemplated by this disclosure that can have nine total locking flaps 50 with three inward flaps 92 and six outward flaps 94. The locking flaps 50 can be arranged so that each inward flap 92 is adjacent to two outward flaps 94 and each outward flap 94 adjacent to one inward flap 92 and one other outward flap 94. The outward flaps 94 can include a first outward flap, a second outward flap, and a third outward flap.

The first outward flap can have a first length dimension, the second outward flap can have a second length dimension, and the third outward flap can have a third length dimension. The first length dimension, the second length dimension, and the third length dimension can be longitudinal lengths of the first outward flap, the second outward flap, and the third outward flap, respectively.

The first length dimension can be measured from the base of the first outward flap to the tip or terminal end of the first outward flap. The base of the first outward flap can be the portion of the first outward flap connected to the upper portion 98 of the sleeve frame 48. The second length dimension can be measured from the base of the second outward flap to the tip or terminal end of the second outward flap. The base of the second outward flap can be the portion of the second outward flap connected to the upper portion 98 of the sleeve frame 48.

The third length dimension can be measured from the base of the third outward flap to the tip or terminal end of the third outward flap. The base of the third outward flap can be the portion of the third outward flap connected to the upper portion 98 of the sleeve frame 48.

The third length dimension can be greater than the first length dimension but less than the second length dimension. The difference between the second length dimension and the first length dimension can be between, e.g., 0.001 mm and 4.0 mm. The sleeve 42 can have two outward flaps 94 having the first length dimension, another two outward flaps 94 having the second length dimension, and yet another two outward flaps 94 having the third length dimension. In one variation, the inward flaps 92 can have the same or substantially equivalent length dimension. In other variations, the inward flaps 92 can have differing length dimensions. Each of the inward flaps 92 can have a gap 100 defined along the upper portion 98 of the sleeve frame 48 at the terminal end of the inward flaps 92.

Although several variations of the sleeve 42 having different number and arrangement of locking flaps 50 are shown, it should be understood by one of ordinary skill in the art that other variations of the sleeve 42 are contemplated by this disclosure including sleeves 42 having less than eight locking flaps 50 or more than nine locking flaps 50. In addition, it is contemplated by this disclosure that all of the locking flaps 50 of a singular sleeve 42 can have a different length dimension and none of the locking flaps 50 of this singular sleeve 42 can be of the same or equivalent lengths.

FIG. 8A illustrates a top plan view of a variation of the prosthesis assembly 40. As shown in FIG. 8A, the prosthesis assembly 40 can include an oral appliance 28 adjustably locked to a variation of the abutment assembly 44 via the sleeve 42 and the coping 46 coupled to the oral appliance 28. The sleeve 42 can be adjustably locked to both the abutment assembly 44 and the coping 46 via one or more locking flaps 50.

FIGS. 8B and 8C illustrate cross-sectional side views of variations of the prosthesis assembly 40 taken along lines A-A and B-B shown in FIG. 8A. FIGS. 8B and 8C illustrate that the coping 46 can have a coping undercut 150 and the abutment assembly 44 can have a plurality of abutment undercuts 152. The coping undercut 150 can be a groove or indentation extending radially into an inner surface of the coping 46. The coping undercut 150 can be defined along a lower portion of the coping 46 proximal to a base of the coping 46. The abutment undercuts 152 can be grooves or indentations extending radially inward relative to a lateral surface of the frustum 56. The abutment undercuts 152 can include undercuts positioned at the top of the frustum 56 and at the bottom of the frustum 56. The abutment undercuts 152 will be described in more detail in the sections that follow. For illustrative purposes, FIGS. 8B and 8C emphasize the abutment undercuts 152 at the top of the frustum 56.

FIGS. 8B and 8C illustrate cross-sectional side views of the prosthesis assembly 40 taken along the same lines A-A and B-B shown in FIG. 8A. The prosthesis assembly 40 of FIGS. 8B and 8C includes the sleeve 42 having locking flaps 50 with differing length dimensions. FIGS. 8B and 8C show the first set of outward flaps 94 and the second set of longer outward flaps 94 are both locked on the coping undercut 150.

One benefit of a sleeve 42 having locking flaps 50, including inward flaps 92 and outward flaps 94, of differing lengths is to provide tolerance for mistakes committed by the dental practitioner in placing the oral appliance 28 onto the abutment assembly 44. Another benefit of the sleeve 42 having locking flaps 50 of differing lengths is to account for non-uniformity or differences in the size and shape of surface features or components defining the abutment assembly 44 or coping 46.

Figure 9:
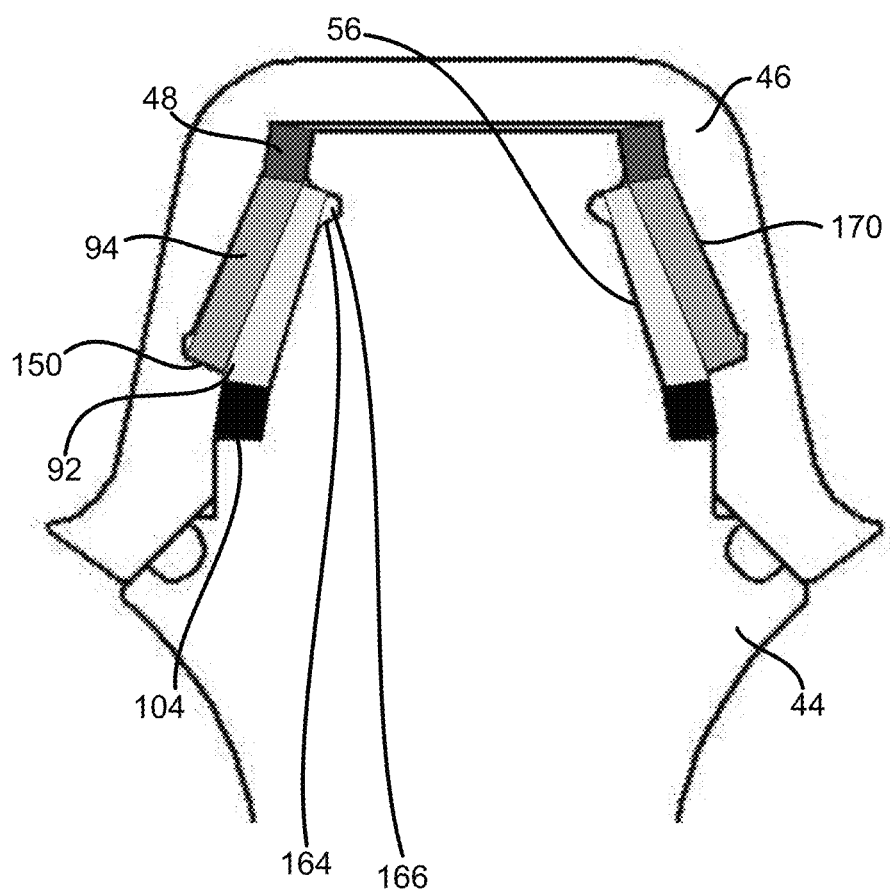
FIG. 9 illustrates a cross-sectional side view of a variation of a coping covering an abutment assembly.

FIG. 9 illustrates a cross-sectional side view of a variation of the coping 46 covering the abutment assembly 44. The abutment assembly 44 can be defined by the frustum 56 along the upper abutment portion 52. The frustum 56 can have a frustum surface 160, a frustum base 162, and a frustum top 164. The frustum surface 160 can be a lateral or side surface of the frustum 56. The frustum surface 160 can be in between the frustum base 162 and the frustum top 164.

The abutment assembly 44 can be defined by a plurality of abutment undercuts 152 along the upper abutment portion 52. The abutment undercut 152 can include a cornice undercut 166 and a base undercut 168. The cornice undercut 166 can be defined at the frustum top 164. The cornice undercut 166 can extend circumferentially around a perimeter of the frustum top 164. One or more inward flaps 92 of the sleeve 42 can lock against an edge adjoining the cornice undercut 166 when the sleeve 42 is in the locking configuration 90. The inward flaps 92 can lock against the edge adjoining the cornice undercut 166 when the terminal ends of the inward flaps 92 pushes against or contacts the edge to prevent the sleeve 42 from being longitudinally displaced from the frustum 56 of the abutment assembly 44. For example, the inward flaps 92 can lock against an edge adjoining the cornice undercut 166 to prevent the sleeve 42 from slipping off the abutment assembly 44.

The base undercut 168 can be defined at the frustum base 162. The base undercut 168 can extend circumferentially around a perimeter of the frustum base 162. The bottom edge 104 of the sleeve frame 48 can push against or contact a base edge extending from the base undercut 168 when the inward flaps 92 of the sleeve 42 lock against the edge adjoining the cornice undercut 166. The cornice undercut 166 and the base undercut 168 will be discussed in more detail in the sections that follow.

As shown in FIG. 9, the coping 46 can cover the abutment assembly 44. The coping 46 can be defined by an inner surface 170. The inner surface 170 can be a surface of the underside of the coping 46. The inner surface 170 can be a tapered underside surface of the coping 46. The inner surface 170 of the coping 46 can be in contact with portions of the sleeve 42, the abutment assembly 44, or a combination thereof.

The inner surface 170 can be defined by a coping undercut 150. The coping undercut 150 can extend around the inner surface 170 of the coping 46. One or more outward flaps 94 of the sleeve 42 can lock against the coping undercut 150. The outward flaps 94 can lock against the coping undercut 150 when the terminal ends of the outward flaps 94 pushes against or contacts the coping undercut 150. The outward flaps 94 can lock against the coping undercut 150 to removably and adjustably couple the coping 46 to the abutment assembly 44. The outward flaps 94 can also lock against the coping undercut 150 to prevent the coping 46 from being longitudinally displaced from the abutment assembly 44 covered by the sleeve 42. The coping undercut 150 will be discussed in more detail in the sections that follow.

Figures 10A, 10B, 10C:
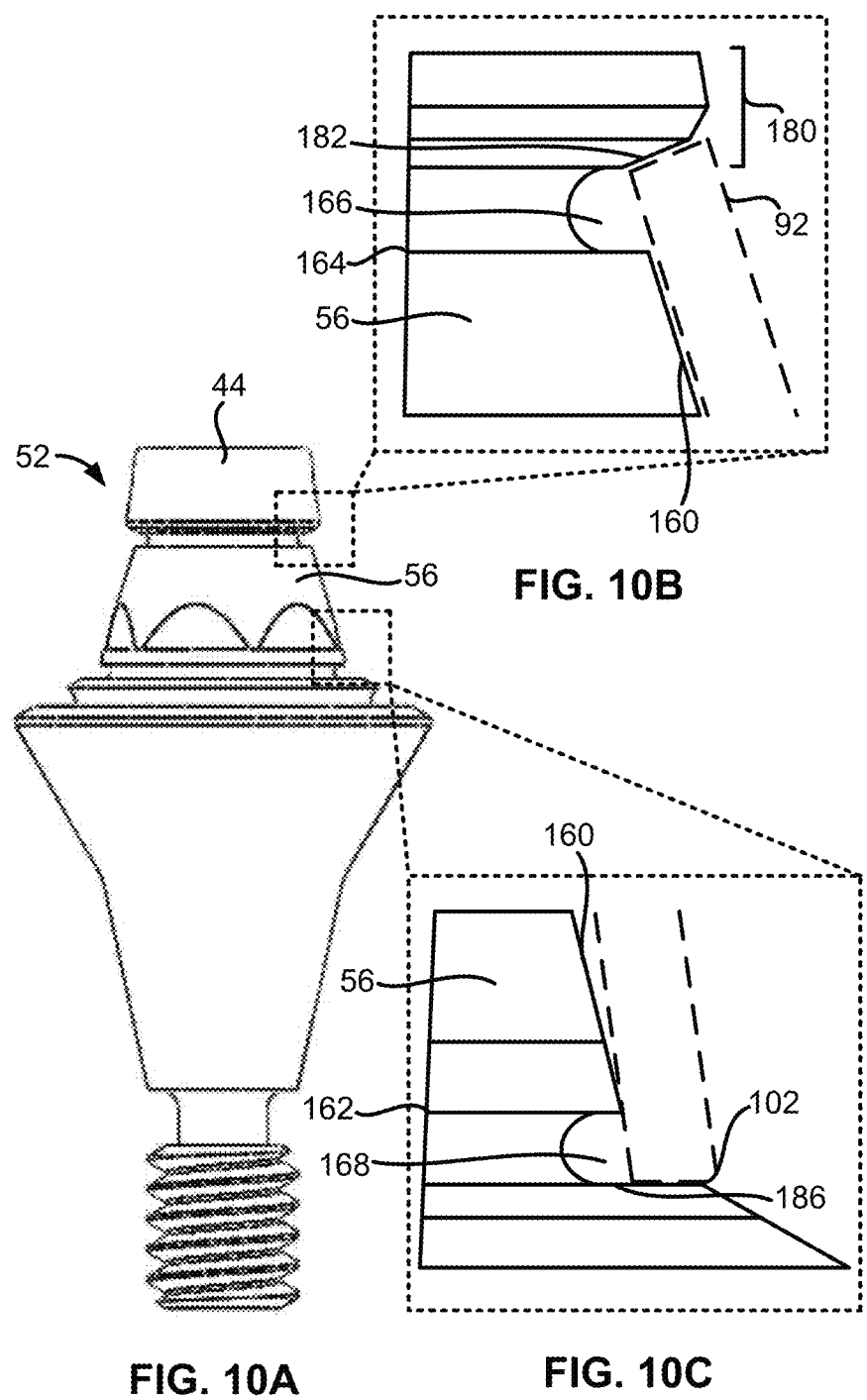
FIG. 10A illustrates a variation of an abutment assembly.
FIG. 10B is an inset of a close up of a portion of the abutment assembly of FIG. 10A.
FIG. 10C is an inset of a close up of another portion of the abutment assembly of FIG. 10A.

FIG. 10A illustrates a variation of the abutment assembly 44. FIG. 10B is an inset of a close up of a portion of the abutment assembly 44 of FIG. 10A. FIG. 10B illustrates that the abutment assembly 44 can have a cornice portion 180 along the upper abutment portion 52. The cornice portion 180 can be an overhang or annular portion protruding radially outward relative to the frustum surface 160. The cornice portion 180 can include one or more edges or surfaces of the upper abutment portion 52. As shown in FIG. 10B, the cornice portion 180 can include a chamfered edge 182. The chamfered edge 182 can be a beveled, pitched, or sloped edge of the cornice portion 180. The chamfered edge 182 can have a chamfer angle of up to 80° relative to a transverse horizontal plane.

The chamfered edge 182 can act as a receiving surface for the ends or terminal portions of the inward flaps 92 of the sleeve 42. The chamfered edge 182 can offer a surface aligned with the ends or terminal portions of the inward flaps 92 as the inward flaps 92 curve or bend radially inward relative to the lateral surface of the sleeve frame 48. In other variations not shown in the figures but contemplated by this disclosure, the cornice portion 180 can include a flat or horizontal edge and the flat or horizontal edge can also act as a receiving surface for the ends or terminal portions of the inward flaps 92 of the sleeve 42. In some variations, the chamfered edge 182 can be an abraded or friction-inducing surface.

The chamfered edge 182 can adjoin a portion of the cornice undercut 166. For example, the chamfered edge 182 can act as a transitional edge or surface between a surface of the cornice undercut 166 and the rest of the cornice portion 180. As depicted in FIG. 10B, the cornice undercut 166 can have a semi-circular or semi-oval cross-section. The cornice undercut 166 can extend radially inward relative to or further inward than the frustum surface 160. For example, the semi-circular cutout of the cornice undercut 166 can extend radially inward relative to the frustum surface 160. The portion of the abutment assembly 44 defined by the cornice undercut 166 can be substantially shaped as a hyperboloid. In other variations not shown in the figures but contemplated by the disclosure, the cornice undercut 166 can have a cross-section of different shapes, e.g. triangular or rectangular.

The cornice undercut 166 adjoining the chamfered edge 182 can assist the inward flaps 92 in more securely coupling the sleeve 42 to the abutment assembly 44 when the sleeve 42 is in the locking configuration 90. The extra space provided by the cornice undercut 166 can allow the end or terminal edge of the inward flap 92 to contact or push against the chamfered edge 182 without the frustum surface 160 deflecting the corner or end of the inward flap 92 away from the cornice portion 180. For example, the cornice undercut 166, the chamfered edge 182, or a combination thereof can assist the inward flaps 92 in more securely coupling the sleeve 42 to the abutment assembly 44 when the sleeve 42 moves as a result of forces exerted on the patient's dentition during normal wear.

The chamfered edge 182 can have a plurality of inward flaps 92 locked against the chamfered edge 182. For example, the chamfered edge 182 can have inward flaps 92 of different lengths locked or pushing against the chamfered edge 182. The inward flaps 92 can lock against the chamfered edge 182 at the same time that the outward flaps 94 lock against the coping undercut 150.

FIG. 10C is an inset of a close up of another portion of the variation of the abutment assembly 44 of FIG. 10A. FIG. 10C illustrates that the abutment assembly 44 can have a base edge 186. In one variation, the base edge 186 can be a substantially flat or horizontal edge. In other variations, the base edge 186 can be an angled or sloped edge having a slope angle of up to 80° relative to a transverse horizontal plane.

The base edge 186 can act as a receiving surface for the ends or terminal portions of the bottom edge 104 of the sleeve frame 48. The base edge 186 can offer a surface aligned with the bottom edge 104 of the sleeve frame 48. In some variations, the base edge 186 can be an abraded or friction-inducing surface.

The base edge 186 can adjoin a portion or surface of the base undercut 168. As depicted in FIG. 10C, the base undercut 168 can have a semi-circular or semi-oval cross-section. The portion of the abutment assembly 44 defined by the base undercut 168 can be substantially shaped as a hyperboloid. The base undercut 168 can extend radially inward relative to or further inward than the frustum surface 160. For example, the semi-circular cutout of the base undercut 168 can extend radially inward relative to the frustum surface 160. In other variations not shown in the figures but contemplated by the disclosure, the base undercut 168 can have a cross-section of different shapes, e.g. triangular or rectangular.

The base undercut 168 adjoining the base edge 186 can allow a dental professional to more securely couple the sleeve 42 to the abutment assembly 44 when the sleeve 42 is in the locking configuration 90. The extra space provided by the base undercut 168 can allow the bottom edge 104 to contact or push against the base edge 186 without the frustum surface 160 deflecting the bottom edge 104 away from the frustum base 162. In addition, the base undercut 168, the base edge 186, or a combination thereof can allow a dental professional to more securely couple the sleeve 42 to the abutment assembly 44 when the sleeve 42 moves as a result of forces exerted on the patient's dentition during normal wear.

Figure 11:
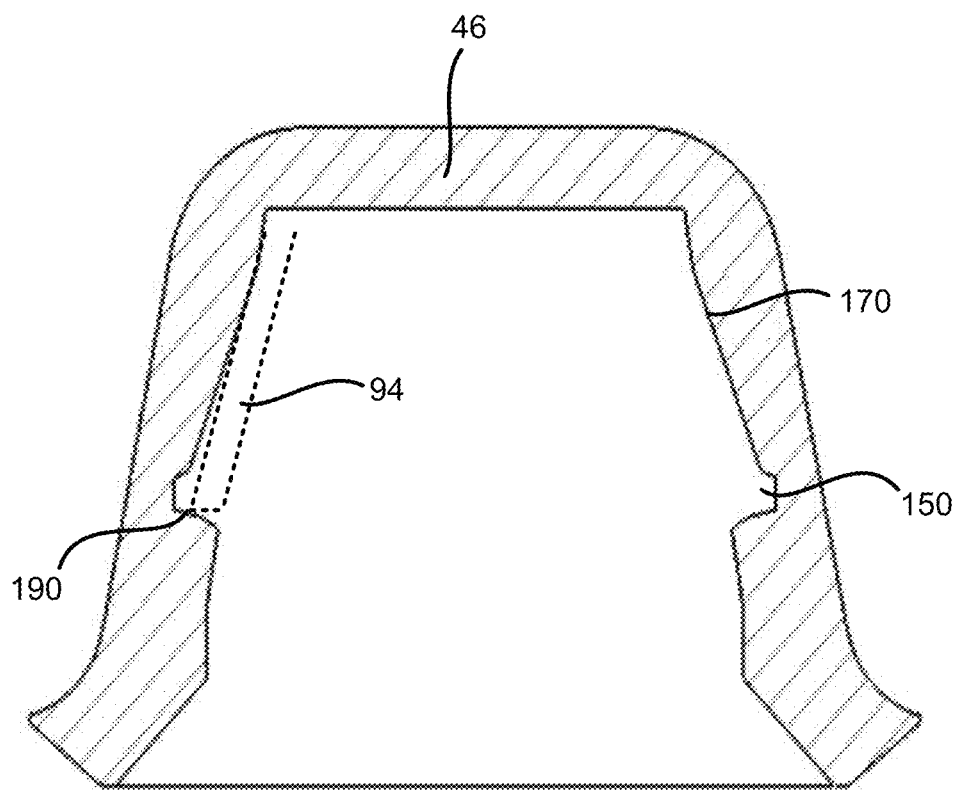
FIG. 11 illustrates a cross-sectional side view of a variation of a coping of the prosthesis assembly.

FIG. 11 illustrates a cross-sectional side view of a variation of the coping 46. The inner surface 170 of the coping 46 can be a tapered or frustoconical-shaped surface on the underside of the coping 46. The coping undercut 150 can extend radially outward relative to the center of the coping 46 and into the inner surface 170. For example, the coping undercut 150 can be a circular or annular groove circumferentially extending into the inner surface 170.

The coping undercut 150 can be defined by an inner edge 190. The inner edge 190 can be an edge or surface created by the coping undercut 150 along the inner surface 170 of the coping 46. In one variation, the inner edge 190 can be a curved or filleted edge having a radius. In another variation, the inner edge 190 can be a substantially horizontal edge or surface. In yet another variation, the inner edge 190 can be a chamfered edge or angled edge. In some variations, the inner edge 190 can be an abraded or friction-inducing surface.

The inner edge 190 can act as a receiving surface for the ends or terminal portions of the outward flaps 94 of the sleeve 42. The inner edge 190 can offer a surface aligned with the ends or terminal portions of the outward flaps 94 as the outward flaps 94 curve or bend radially outward relative to the lateral surface of the sleeve frame 48. The outward flaps 94 can lock against the inner edge 190 when the terminal ends of the outward flaps 94 pushes against or contacts the inner edge 190. The outward flaps 94 can lock against the inner edge 190 to removably and adjustably couple the coping 46 to the abutment assembly 44. The outward flaps 94 can also lock against the inner edge 190 of the coping undercut 150 to prevent the coping 46 from being longitudinally displaced from the abutment assembly 44 covered by the sleeve 42.

The coping undercut 150 can assist the outward flaps 94 in more securely retaining the coping 46 to the abutment assembly 44 when the sleeve 42 is in the locking configuration 90. The extra space provided by the coping undercut 150 can allow the ends or terminal edges of the outward flaps 94 to contact or push against the inner edge 1190 without the inner surface 170 deflecting the corners or ends of the outward flaps 94 away from the inner edge 190.

The inner edge 190 of the coping undercut 150 can have a plurality of outward flaps 94 locked against the inner edge 190. For example, the inner edge 190 can have outward flaps 94 of different lengths locked or pushing against the inner edge 190.

Figures 12A, 12B, 12C:
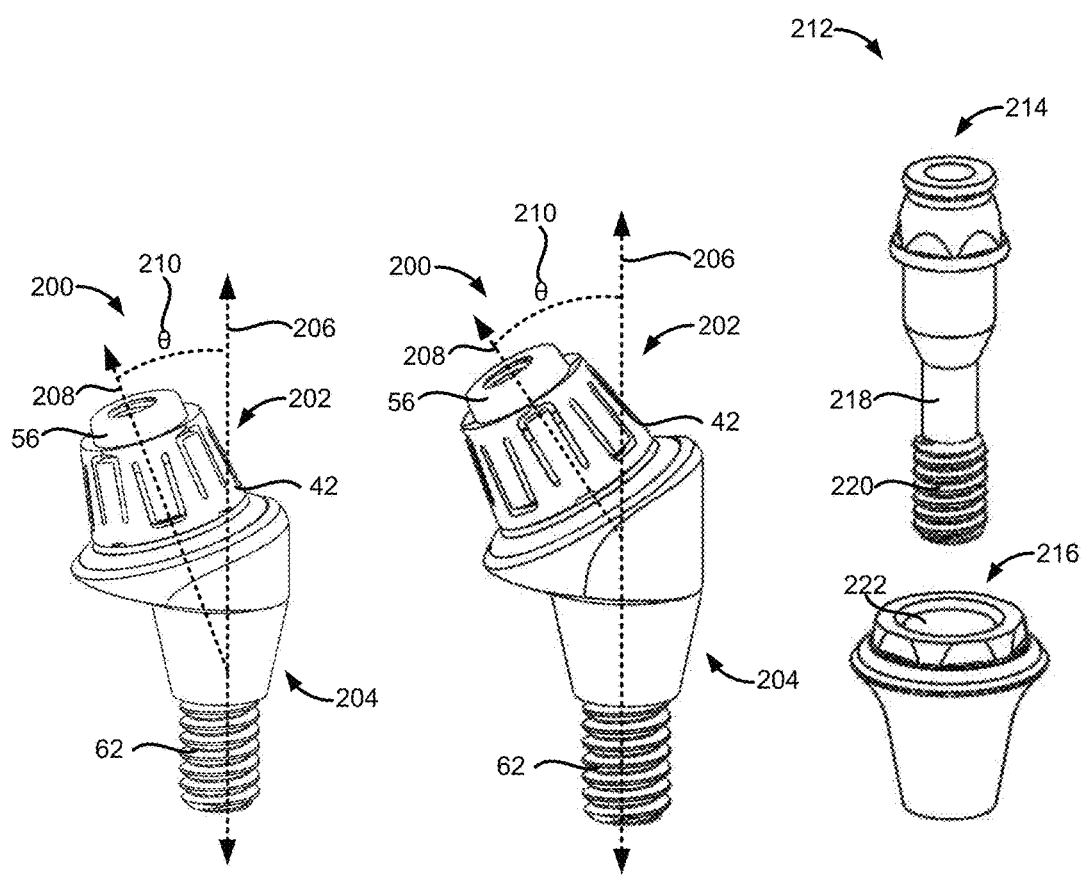
FIG. 12A illustrates a variation of an angled abutment assembly with a sleeve positioned on the angled abutment assembly.
FIG. 12B illustrates another variation of an angled abutment assembly with a sleeve positioned on the angled abutment assembly.
FIG. 12C illustrates a variation of a two-piece abutment assembly.

FIGS. 12A and 12B illustrate variations of an angled abutment assembly 200 with variations of the sleeve 42 positioned on the angled abutment assembly 200. The angled abutment assembly 200 can comprise an upper abutment portion 202 and a lower abutment portion 204. The lower abutment portion 204 can comprise a threaded pin 62. The threaded pin 62 can be inserted or screwed into a threaded cavity of the implant 18 to secure the angled abutment assembly 200 to the implant 18. FIGS. 12A and 12B also illustrate a thread longitudinal axis 206 and a frustum longitudinal axis 208. The thread longitudinal axis 206 and the frustum longitudinal axis 208 can be used to orient the angled abutment assembly 200. The thread longitudinal axis 206 can run along the length of the threaded pin 62 and the frustum longitudinal axis 208 can run along the length of the frustum 56. The upper abutment portion 202 can be angled relative to the lower abutment portion 204. For example, the frustum 56 of the angled abutment assembly 200 can be angled relative to the thread 62 of the angled abutment assembly 200. More specifically, the thread longitudinal axis 206 can form an angle 210, e.g., θ, with respect to the frustum longitudinal axis 208.

The angle 210 can range from 1° to 60°. For example, the angled abutment assembly of FIG. 12A can have an angle 210 of approximately 17° and the angled abutment assembly of FIG. 12B can have an angle 210 of approximately 30°. The angle 210 can vary depending on the desired angulation of the oral appliance 28 relative to the implant 18.

FIGS. 12A and 12B illustrate that frustum 56 of the angled abutment assembly 200 can be covered by the sleeve 42. For example, any of the sleeves 42 depicted in FIG. 2, 3A, 4A, 5A, 5B, 6, 7A, or 7B can be positioned on the frustum 56 to lock an oral appliance 28 to the angled abutment assembly 200 via a coping 46 attached to the oral appliance 28.

The angled abutment assembly 200 can be fabricated from the same material(s) as the abutment assembly 44 including any number of biocompatible materials, e.g., metals, metal alloys, polymers, or composites thereof.

FIG. 12C illustrates a variation of a two-piece abutment assembly 212. The two-piece abutment assembly 212 can comprise an upper abutment portion 214 and a lower abutment portion 216. The upper abutment portion 214 can comprise an extender shaft 218 and an extension threaded portion 220. The extender shaft 218 can raise the height of the remainder of the upper abutment portion 214 to account for differences in the topography of the gingiva 14 of patients. The lower abutment portion 216 can comprise a receiving cavity 222. The receiving cavity 222 can be a threaded cavity for receiving the extension threaded portion 220. The lower abutment portion 216 can also comprise a threaded pin for coupling to the implant 18.

The two-piece abutment assembly 212 can be fabricated from the same material(s) as the abutment assembly 44 or the angled abutment assembly 200 including any number of biocompatible materials, e.g., metals, metal alloys, polymers, or composites thereof.

Figure 13A:
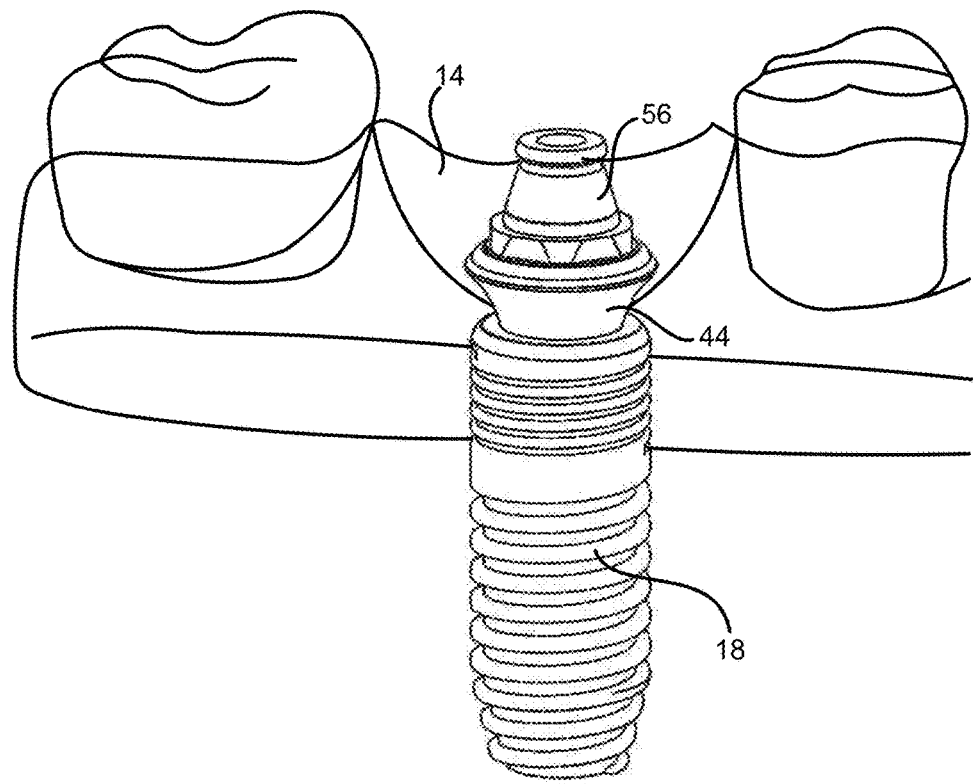
FIGS. 13A to 13F illustrate a method of placing and removing a crown from an abutment assembly.

FIGS. 13A to 13F illustrate a method of placing and removing an oral appliance 28 from a variation of the abutment assembly 44. FIG. 13A illustrates that an abutment assembly 44 can be coupled to an anchoring implant 18 implanted within an oral cavity of a patient. At least part of the abutment assembly 44 can extend beyond the gingiva 14 of the patient once the abutment assembly 44 is coupled to the anchoring implant 18.

Figure 13B:
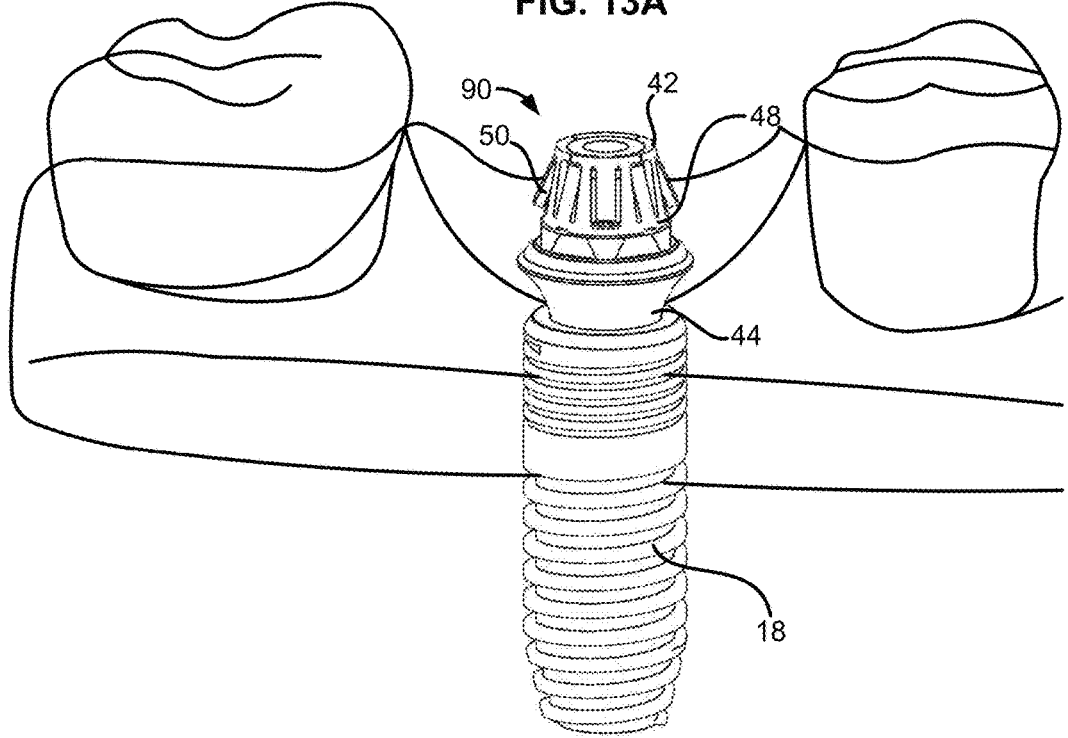

FIG. 13B illustrates that a variation of the sleeve 42 can be coupled to the abutment assembly 44. The sleeve 42 can be any of the sleeves 42 depicted in FIG. 2, 3A, 4A, 5A, 5B, 6, 7A, or 7B. For example, the sleeve 42 can have locking flaps 50 of differing lengths such as the locking flaps 50 depicted in FIGS. 7A and 7B. In the example variation shown in FIG. 13B, the sleeve 42 can be positioned on the frustum 56 of the abutment assembly 44 in the locking configuration 90. In this variation, the one or more inward flaps 92 can project radially inward relative to the sleeve frame 48. The inward flaps 92 can lock against chamfered edge 182 of the abutment assembly 44. The bottom edge 104 of the sleeve frame 48 can also push against the base edge 186 of the abutment assembly 44 to couple or secure the sleeve 42 to the abutment assembly 44. FIG. 13B also illustrates that one or more outward flaps 94 can project radially outward relative to the sleeve frame 48 when the sleeve 42 is in the locking configuration 90.

Figure 13C:
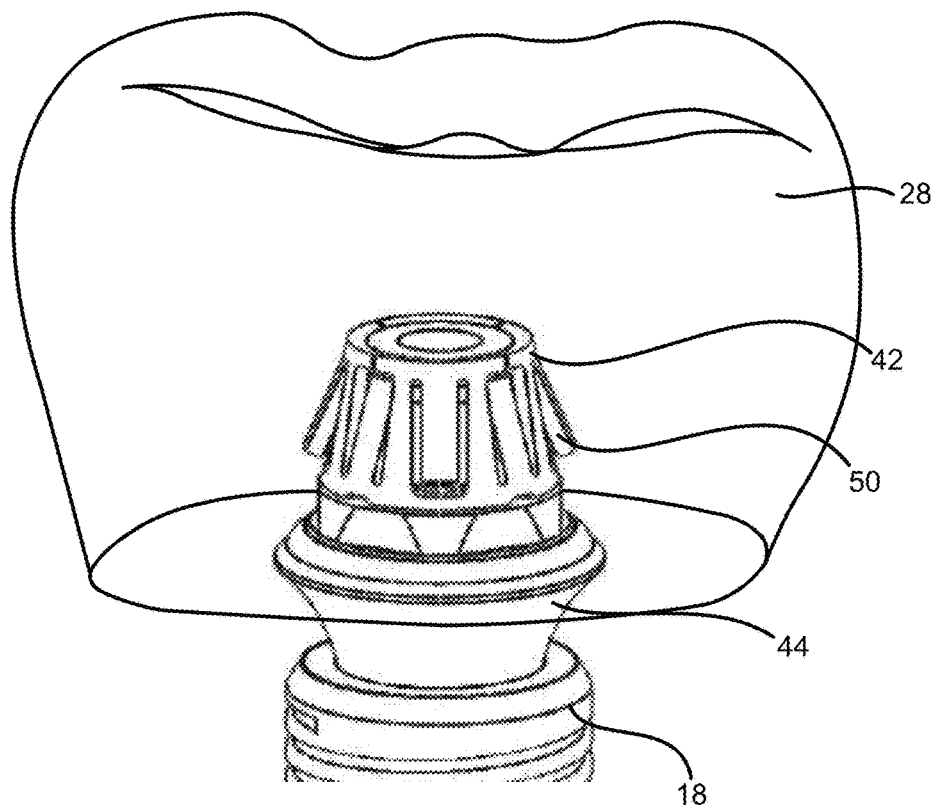

FIG. 13C illustrates that an oral appliance 28, e.g., a crown, coupled to a coping 46 can be placed onto the sleeve 42 in the locking configuration 90 to secure the oral appliance 28 to the abutment assembly 44. The outward flaps 94 of the sleeve 42 can lock against the inner edge 190 of the coping undercut 150 to prevent the oral appliance 28 from being vertically displaced from the abutment assembly 44.

Figure 13D:
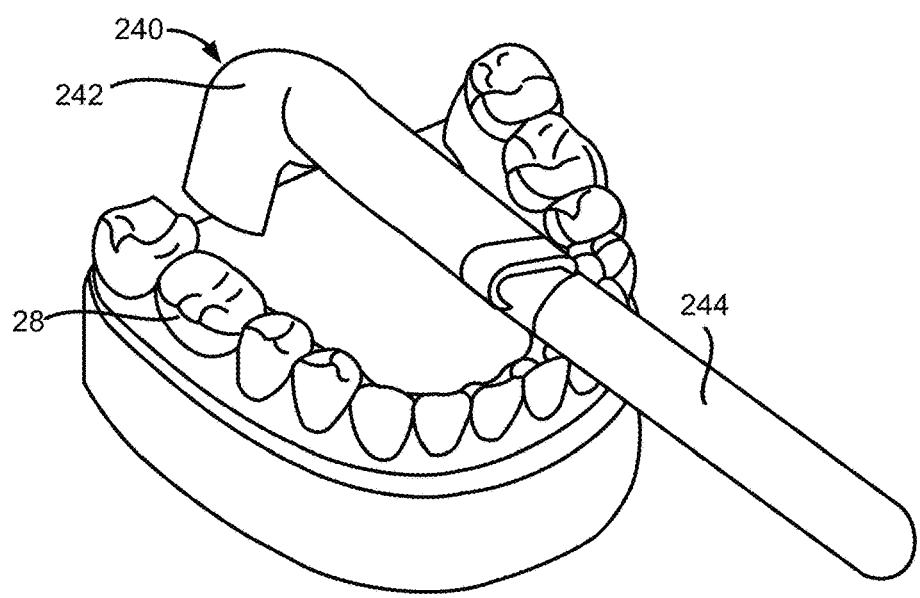

FIG. 13D illustrates an actuator unit 240 in the process of being deployed on the oral appliance 28 coupled to the abutment assembly 44 by the sleeve 42. The actuator unit 240 can be a handheld or portable unit. The actuator unit 240 can comprise an actuator head 242 and an actuator shaft 244. The actuator unit 240 can also comprise a power source not shown in the figures.

Figure 13E:
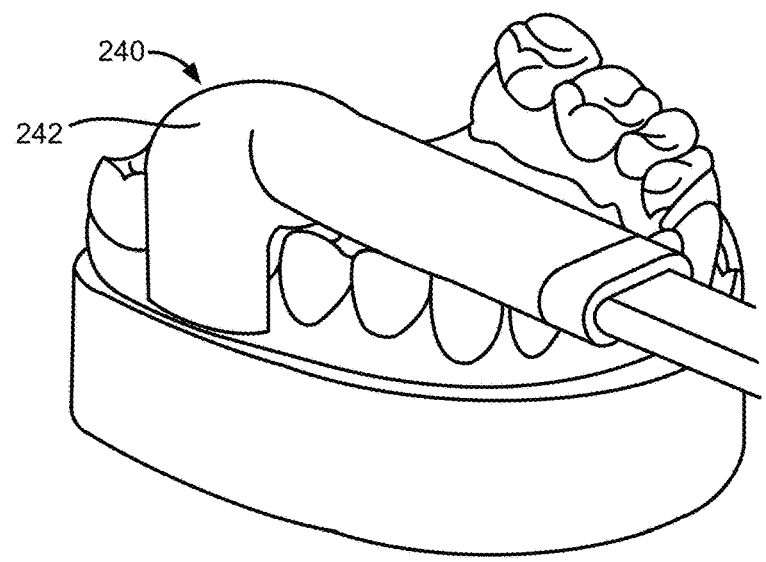

FIG. 13E illustrates the actuator head 242 of the actuator unit 240 placed over the oral appliance 28. The actuator unit 240 can comprise an inductive heating assembly comprising a controller-like variable output oscillator circuit, a conductor, and one or more coils set apart in apposition and at a distance from one another. The controller-like variable output oscillator circuit can be coupled to the conductor and the coils. The distance or gap between the coils can define a receiving channel which can be sized to be positioned over an oral appliance 28, e.g., the crown shown in FIGS. 13C and 13D. When the abutment assembly 44, the sleeve 42, and the oral appliance 28 is positioned within the receiving channel of the actuator head 242, the controller-like variable output oscillator circuit can send an alternating current through the conductor to the coils to generate an alternating magnetic field between the coils. The alternating magnetic field can cause eddy currents to form in at least part of the abutment assembly 44, the coping 46, the sleeve 42, or a combination thereof. The eddy currents can cause at least part of the abutment assembly 44, the coping 46, the sleeve 42, or a combination thereof to heat up, thereby activating the shape memory material of the locking flaps 50 to initiate their shape change and cause the sleeve 42 to actuate into the low-profile configuration 70 of FIG. 13F.

Figure 13F:
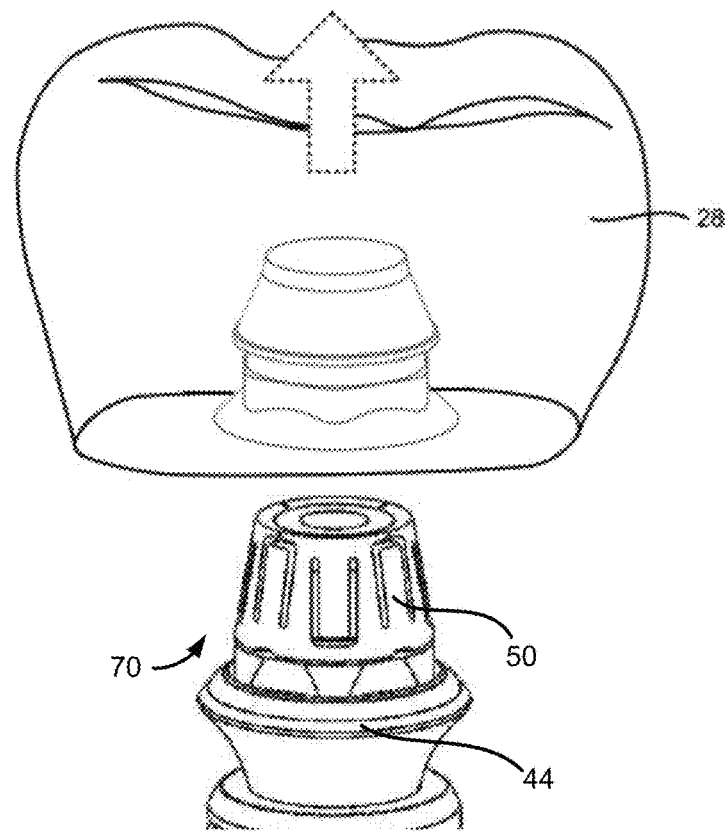

The frequency of the alternating current and the magnetic field can be set between, e.g., 1 kHz and 1 MHz, depending on the size and configuration of the locking flaps 50 and the activation time. The power consumption can range between, e.g., 1 W to 150 W. The induction heating assembly can be the induction heating assembly described in U.S. Pat. No. 9,168,111, which is herein incorporated by reference in its entirety. The actuator head 242 can also comprise a disposable or one-time use tip for covering or protecting the actuator head 242. As illustrated in FIG. 13F, once the sleeve 42 is actuated into the low-profile configuration 70, the coping 46 coupled to the oral appliance 28 can be uncoupled from the abutment assembly 44 and the oral appliance 28 can be lifted off of the abutment assembly 44.

Figure 14:
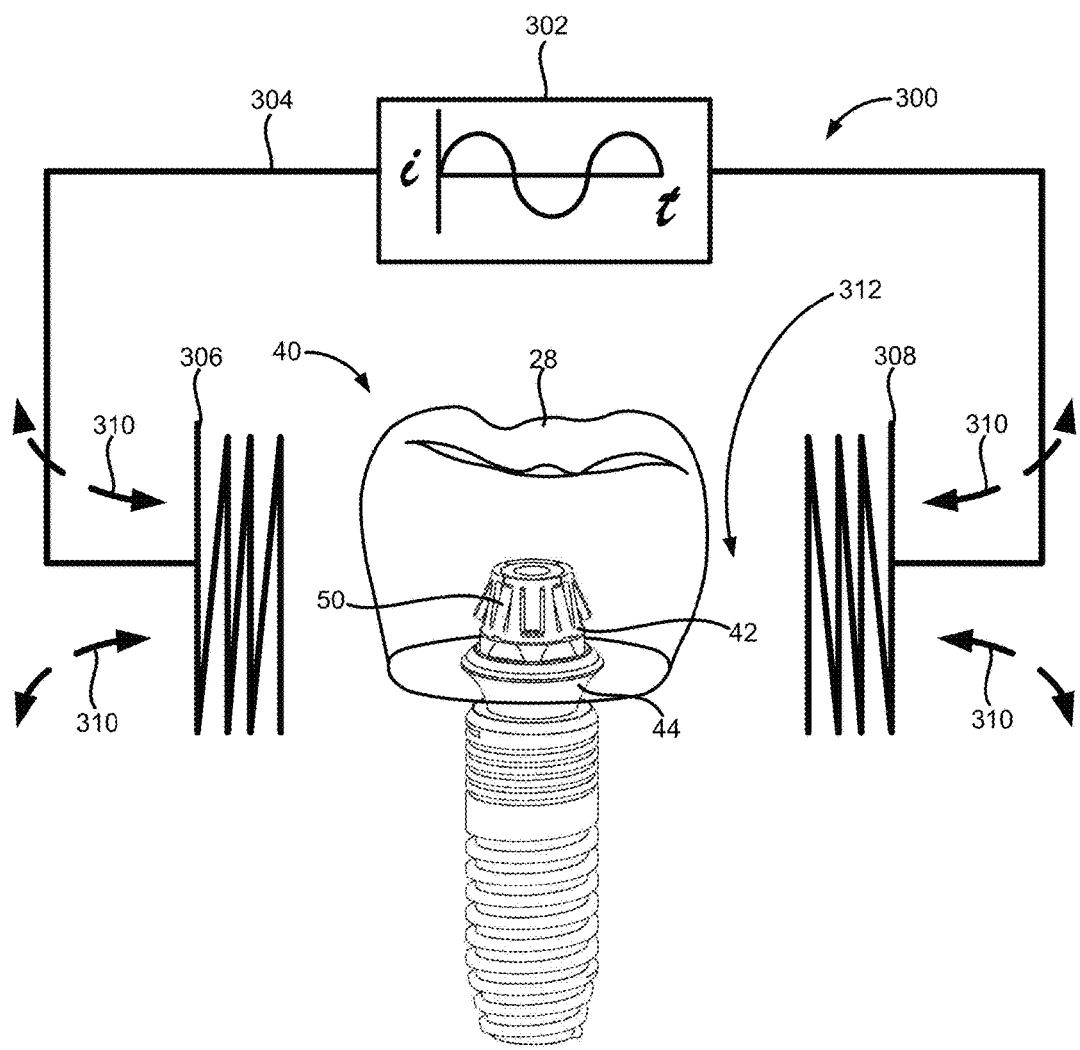
FIG. 14 illustrates an example of energy being applied via a power source and controller to a variation of the prosthesis assembly.

FIG. 14 illustrates an example of energy being applied via an inductive heating assembly 300. The inductive heating assembly 300 can be regulated with a controller-like variable oscillator circuit 302 which sends an alternating current i through conductor 304 to one or more coils 306 and 308 which then generates an alternating magnetic field 310 between the coils 306 and 308 which may be set apart in apposition and at a distance from one another. The distance between the coils 306 and 308 may define a receiving channel 312 which is sized to be positioned over, adjacent to, or in proximity to the oral appliance 28. The inductive heating assembly 300 may be positioned upon or in proximity to the oral appliance 28 within the user's mouth.

With the oral appliance 28, as well as the abutment assembly 44 and the sleeve 42, positioned within receiving channel 312, the alternating magnetic field 310 can be created between coils 306 and 308 to form eddy currents in the one or more locking flaps 50. These eddy currents, which can also be described as the movement of electrons in the material, causes the material to heat up due to electrical resistance and thus activates the shape memory material to initiate their shape change. The frequency of the alternating current i and the magnetic field can be set between, e.g., 1 kHz and 1 MHz, depending on the size and configuration of the locking flaps 50 and the targeted activation time. Moreover, the power consumption may range between about, e.g., 1 W to 150 W. As described above, the inductive heating assembly 300 can be configured as a portable hand-held unit or as a larger non-portable unit. Additional details and examples of an inductive heating assembly are further shown in U.S. Pat. No. 6,710,314, which is incorporated herein by reference in its entirety.

In one variation, the inductive heating assembly 300 can be configured into a handheld actuation unit such as the actuation unit 240 of FIGS. 13D and 13E or a larger non-portable unit. The heating time can range from, e.g., 0.1 to 60 seconds or longer. The prosthesis assembly 40 can be heated without any direct contact between components of the inductive heating assembly 300 and the prosthesis assembly 40.

The applications of the devices and methods discussed above are not limited to the securement of crowns, bridges, or dentures but may include any number of further treatment applications where the securement and adjustability of devices within a patient may be utilized. Moreover, such devices and methods may be applied to other treatment sites within the body. Modification of the above-described assemblies and methods for carrying out the disclosure, combinations between different variations as practicable, and variations of aspects of the invention that are obvious to those of skill in the art are intended to be within the scope of the claims.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the methods disclosed do not require the particular order described to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this disclosure belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A securement assembly for adjustably retaining an oral appliance in an oral cavity, comprising:
    a sleeve comprising a sleeve frame, a plurality of locking flaps comprising a first locking flap and a second locking flap, wherein the sleeve defines a lumen therethrough,
        wherein the first locking flap has a first length dimension and the second locking flap has a second length dimension,
        wherein the first length dimension is different from the second length dimension;
    an abutment assembly comprising a frustum having a frustum surface and configured to receive the lumen of the sleeve,
        wherein the abutment assembly is defined by a first undercut extending radially inward relative to a portion of the frustum surface, wherein the portion of the frustum surface is configured to be in contact with the plurality of locking flaps; and
    wherein the first locking flap and the second locking flap project radially inward relative to the sleeve frame for locking against a first edge of the abutment assembly adjoining the first undercut.

2. The securement assembly of claim 1, wherein the abutment assembly further comprises a second undercut extending radially inward relative to the frustum surface at a base of the frustum and wherein an edge of the sleeve frame contacts a second edge of the abutment assembly adjoining the second undercut when at least one of the locking flaps is locked against the first edge.

3. The securement assembly of claim 1, wherein the abutment assembly comprises a thread pin and a portion of the abutment assembly is angled relative to the thread pin.

4. The securement assembly of claim 1, wherein the first edge is chamfered.

5. The securement assembly of claim 1, wherein the first undercut has a semi-circular or semi-oval cross-section.

6. A securement assembly for adjustably retaining an oral appliance in an oral cavity, comprising:
    a sleeve comprising a sleeve frame and a plurality of locking flaps comprising a first locking flap comprising a first locking flap terminal end and a second locking flap comprising a second locking flap terminal end,
        wherein the first locking flap has a first length dimension and the second locking flap has a second length dimension,
        wherein the first length dimension is different from the second length dimension;
    a coping having a tapered inner surface, wherein the coping is defined by a coping undercut extending radially outward relative to the tapered inner surface; and
    wherein at least one of the first locking flap and the second locking flap project radially outward relative to the sleeve frame for locking against an edge of the coping undercut.

7. A method of adjustably retaining an oral appliance in an oral cavity, comprising:

securing an abutment assembly in an oral cavity of a patient such that an abutment portion extends beyond the gingiva of the patient, wherein the abutment assembly comprises a frustum having a frustum surface;

coupling a sleeve comprising a sleeve frame to the abutment portion, wherein the sleeve comprises a plurality of inwardly projecting locking flaps and a plurality of outwardly projecting locking flaps, wherein the inwardly projecting locking flaps further comprise a first locking flap and a second locking flap, wherein the first locking flap has a first length dimension, the second locking flap has a second length dimension different from the second length dimension, wherein the abutment assembly is defined by a first undercut extending radially inward relative to a portion of the frustum surface, wherein the portion of the frustum surface is configured to be in contact with the plurality of inwardly projecting locking flaps; and positioning the oral appliance upon the abutment portion and locking the oral appliance to the abutment assembly when the plurality of outwardly projecting locking flaps push against an edge of a coping attached to the oral appliance.

8. The method of claim 7, further comprising:

actuating the plurality of outwardly projecting locking flaps to retract the plurality of outwardly projecting locking flaps into a low-profile configuration; and removing the oral appliance from the abutment assembly when the sleeve is in the low-profile configuration.

9. The method of claim 8, wherein actuating comprises applying energy to a portion of the sleeve.

10. The method of claim 8, further comprising re-actuating the plurality of outwardly projecting locking flaps such that the plurality of outwardly projecting locking flaps project radially outward relative to the sleeve frame.

* * * * *